(12) United States Patent
Alocilja

(10) Patent No.: US 12,339,276 B2
(45) Date of Patent: Jun. 24, 2025

(54) FUNCTIONALIZED MAGNETIC PARTICLE COMPOSITIONS AND RELATED METHODS

(71) Applicant: BOARD OF TRUSTEES OF MICHIGAN STATE UNIVERSITY, East Lansing, MI (US)

(72) Inventor: Evangelyn C. Alocilja, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 1466 days.

(21) Appl. No.: 16/328,324

(22) PCT Filed: Aug. 30, 2017

(86) PCT No.: PCT/US2017/049260
§ 371 (c)(1),
(2) Date: Feb. 26, 2019

(87) PCT Pub. No.: WO2018/044966
PCT Pub. Date: Mar. 8, 2018

(65) Prior Publication Data
US 2021/0164970 A1   Jun. 3, 2021

Related U.S. Application Data

(60) Provisional application No. 62/381,979, filed on Aug. 31, 2016.

(51) Int. Cl.
G01N 33/543 (2006.01)
B82Y 30/00 (2011.01)
(Continued)

(52) U.S. Cl.
CPC . *G01N 33/54333* (2013.01); *G01N 33/54346* (2013.01); *H01F 1/0054* (2013.01); *H01F 1/147* (2013.01); *B82Y 30/00* (2013.01)

(58) Field of Classification Search
CPC ........ G01N 33/54333; G01N 33/54346; H01F 1/0054; H01F 1/147; B82Y 30/00
See application file for complete search history.

(56) References Cited

U.S. PATENT DOCUMENTS 7,776,580 B2   8/2010 Zhang et al.
2009/0123939 A1  5/2009 Alocilja et al.
(Continued)

FOREIGN PATENT DOCUMENTS

EP   1937315 A2   7/2008

OTHER PUBLICATIONS

Lin et al., (Sensors and Actuators B: Chemical vol. 147, Issue 1, May 18, 2010, pp. 343-349). (Year: 2010).*
(Continued)

*Primary Examiner* — Jana A Hines
(74) *Attorney, Agent, or Firm* — MARSHALL, GERSTEIN & BORUN LLP

(57) ABSTRACT

The disclosure relates to functionalized magnetic particle compositions and related methods to extract biological target analytes such as bacteria from samples such as clinical, industrial, or environmental samples. The functionalized magnetic particles can be synthesized in a one-pot method and include a biomimetic binding pair member which permits non-specific binding to one or more biological target analytes, such as when using the functionalized magnetic particles to extract pathogens or other analytes from a sample matrix. The functionalized magnetic particle composition generally includes a magnetic particle core, and a binding pair member bound to an external surface of the magnetic particle core, where the binding pair member is capable of non-specific binding to a plurality of biological target analytes.

27 Claims, 4 Drawing Sheets

(51) Int. Cl.
*H01F 1/00* (2006.01)
*H01F 1/147* (2006.01)

(56) References Cited

U.S. PATENT DOCUMENTS

| | | | |
|---|---|---|---|
| 2011/0171749 A1 | 7/2011 | Alocilja et al. | |
| 2012/0315623 A1 | 12/2012 | Alocilja et al. | |
| 2013/0251641 A1 | 9/2013 | Akhtari et al. | |
| 2014/0303012 A1* | 10/2014 | Alocilja | G01N 33/5434 435/7.37 |

OTHER PUBLICATIONS

Hamer et al., ( Sci Rep. 2015; 5: 8716. Published online Mar. 3, 2015). (Year: 2015).*
Bhusal et al., Nanoparticle-based biosensing of tuberculosis, an affordable and practical alternative to current methods, Biosensors, vol. 9, 11 pp. (2019).
Gordillo-Marroquin et al., Magnetic nanoparticle-based biosensing assay quantitatively enhances acid-fast bacilli count in paucibacillary pulmonary tuberculosis, Biosensors, 8:128, 13 pp. (2018).
Karuppuswami et al., A wireless RFID compatible sensor tag using gold nanoparticle markers for pathogen detection in the liquid food supply chain, IEEE Sensors Letters, 2(2):4 pp. (Jun. 2018).
Matta et al., AuNP-RF sensor: An innovative application of RF technology for sensing pathogens electrically in liquids (SPEL) within the food supply chain, Biosens. Bioelectron., 111:152-8 (Jul. 2018).
Matta et al., Carbohydrate Ligands on Magnetic Nanoparticles for Centrifuge-Free Extraction of Pathogenic Contaminants in Pasteurized Milk, 81(12):1941-9 (Dec. 2018).
Matta et al., Carbohydrate-functionalized nanobiosensor for rapid extraction of pathogenic bacteria directly from complex liquids with quick detection using cyclic voltammetry, IEEE Trans Nanotechnology, 17(5):1006-13 (Sep. 2018).
Matta et al., Emerging nano-biosensing with suspended MNP microbial extraction and EANP labeling, Biosens. Bioelectron., 117:781-93 (Oct. 2018).
Zeeshan et al., Impedance and Magnetohydrodynamic Measurements for Label Free Detection and Differentiation of *E. coli* and *S. aureus* Using Magnetic Nanoparticles, IEEE Trans Nanobioscience, 17(4):443-8 (Oct. 2018).
Lim et al., Alocilja Magnetic Nanoparticles capture *Escherichia coli* O157:H7 isolates. Philippine Journal of Pathology Open Access, 2(2): 47-49 (Nov. 18, 2017).
Dung et al., Preparation and characterization of magnetic nanoparticles with chitosam coating., J. Phys., Conference Series, 187(1): 012036 (2009).
El-Boubbou et al., Glyco-nanomaterials: translating insights from the "sugar-code" to biomedical applications, Curr. Med. Chem., 18(14):2060-78 (2011).
Elbrahiminezhad et al., Impact of amino-acid coating on the synthesis and characteristics of iron-oxide nanoparticles, Bull. Korean Chem. Soc., 33(12):3957-62 (2012).
International Application No. PCT/US17/49260, International Search Report and Written Opinion, dated Nov. 6, 2017.
Park et al., Probing cell-surface carbohydrate binding proteins with dual-modal glycan-conjugated nanoparticles, J. Am. Chem. Soc., 137(18):5961-8 (May 2015).
Alocilja et al., Multifunctional Biomimetic Receptors for Cell Binding and Concentration, Institute of Biological Engineering/NC-1194 Annual Meeting, Greenville, SC, Apr. 7-9, 2016.
Alocilja et al., Synthesis and Verification of Multifunctional Anitmicrobial Glyco-Amino Acid Compounds Against Bacterial Pathogens, Institute of Biological Engineering/NC-1194 Annual Meeting, Greenville, SC, Apr. 7-9, 2016.
Alocilja et al., Development and validation of a nano-enabled self-reporting biosensor (SRB) for rapid screening of microbial agents in the food supply chain, IFT16, Chicago, IL, Jul. 16-19, 2016.
Alocilja et al., Novel Antimicrobial Technologies Against Foodborne Pathogens, International Association for Food Protection Annual Meeting, St. Louis, MO, Jul. 30-Aug. 3, 2016.
Alocilja et al., Global Validation of the Nano-enabled Biosensor for Rapid Diagnosis and Surveillance of Infectious Diseases, 2017 TechConnect World Innovation Conference and Expo, Washington, DC, May 15-17, 2017.

* cited by examiner (A) – various pathogens (B) – Listeria monocytogenes (C) – *Salmonella enteritidis*

(D) – *Mycobacterium smegmatis*

FUNCTIONALIZED MAGNETIC PARTICLE COMPOSITIONS AND RELATED METHODS

CROSS REFERENCE TO RELATED APPLICATION

Priority is claimed to U.S. Application No. 62/381,979 filed Aug. 31, 2016, which is incorporated herein in its entirety.

STATEMENT OF GOVERNMENT INTEREST

None.

BACKGROUND OF THE DISCLOSURE

Field of the Disclosure

The disclosure relates to functionalized magnetic particle compositions that can be used for extracting biological target analytes along with corresponding disease detection based thereon. The functionalized magnetic particles generally include a magnetic particle core and a (non-specific) biomimetic binding pair member bound to the magnetic particle core, where the binding pair member is capable of non-specific binding to one or more biological target analytes.

Background

Bacterial infection is one of the leading causes of death worldwide. Identification of the causative organism is necessary to determine the best treatment option for a patient. Conventional diagnostics mainly rely on culture- or microscopy-based testing for bacterial identification. Culture-based tests require the bacteria to grow on synthetic media and can take up to a week to produce results. Results from microscopy-based tests can be obtained faster than culture-based methods. The acid-fast-bacilli (AFB) test is often performed initially to diagnosis *M tuberculosis* (Mtb). Although this technique is able to provide results typically within a day, the test is not entirely reliable. Not only can false positives arise from the presence of other acid-fast-bacilli, it is estimated that up to half of Mtb cases go undetected by this method. As a result, AFB alone cannot diagnose Mtb infection and culture-based tests are still required to confirm a diagnosis.

To prevent further deterioration of a patient, infections are generally treated before culturing information is available. Once culturing results are obtained patients are often switched to an optimum treatment course. Development of an accurate and consistent biosensor for common bacterial pathogens could expedite laboratory testing and patient diagnosis. Studies have shown that increasing diagnostic speed by a mere 5.2 hours not only allows for a faster switch to an optimum treatment, but reduces the use of unnecessary antimicrobial agents and reduces the average length of hospitalization. This seemingly small change significantly reduces the average cost of patient treatment from $6,677 to $4,927 in the US.

However, the burden of bacterial diseases is primarily felt in poor countries were a visit to a doctor and laboratory testing is a luxury few can afford. In such areas of the world, diagnosing patients can be a challenge due to lack of access to necessary facilities, instruments, or supplies. Culturing requires a controlled environment, specialized media, and takes several days to produce results. If suitable facilities and supplies are available, patient follow up is another issue. Many patients may not be able to return, or chose not to return, when culturing results are available thereby preventing optimal treatment and contributing to disease transmission and increased morbidity. Although microscopy-based tests can provide faster results, they are typically labor intensive, require expensive instruments, and require a skilled technician to perform; all of which can be limiting factors in an economically depressed region. To make the greatest impact in endemic areas of the world, low-cost, low-tech, solutions for diagnosing bacterial infections outside of laboratory conditions are greatly needed.

SUMMARY

The disclosure relates to functionalized magnetic particle compositions and related methods to extract biological target analytes such as bacteria from samples such as clinical, industrial, or environmental samples. The functionalized magnetic particles can be synthesized in a one-pot method and include a biomimetic binding pair member which permits non-specific binding to one or more biological target analytes, such as when using the functionalized magnetic particles to extract pathogens or other analytes (e.g., for subsequent detection thereof) from a sample matrix.

In one aspect, the disclosure relates to a functionalized magnetic particle composition comprising: (a) a magnetic particle core (e.g., generally a nano- or micro-scale particle having a roughly spherical shape); and (b) a (non-specific) binding pair member (e.g., biomimetic binding pair member; such as a glycan) bound to an external surface of the magnetic particle core, the binding pair member being capable of non-specific binding to a plurality of biological target analytes.

In another aspect, the disclosure relates to a functionalized magnetic particle composition comprising: (a) a magnetic particle core comprising at least one of Fe(II) and Fe(III); and (b) a (biomimetic) binding pair member covalently bound to an external surface of the magnetic particle core, the binding pair member comprising an amino carbohydrate moiety capable of non-specific binding to a plurality of biological target analytes; wherein the functionalized magnetic particle composition has a particle size ranging from 100 nm to 1000 nm. The binding pair member can further comprise chitosan and one or more of an oligomeric derivative of chitosan comprising a N-acetylglucosamine moiety, a monomeric N-acetylglucosamine moiety, and a pyrolysis by-product of chitosan.

Various refinements of the functionalized magnetic particle composition are possible.

In a refinement, the magnetic particle core comprises at least one of Fe(II) and Fe(III) (e.g., iron in a +2 or +3 oxidation state, such as an iron(II,III) oxide ($Fe_3O_4$; magnetite), an iron(II) oxide (FeO), or an iron(III) oxide ($\gamma$-$Fe_2O_3$; maghemite), more generally a ferrimagnetic or ferromagnetic material).

In another refinement, the binding pair member comprises at least one of a glycan and glycoconjugate.

In another refinement, the binding pair member comprises at least one of a carbohydrate moiety, an amino derivative thereof (e.g., amino sugar moiety or other carbohydrate/saccharide including an amine group substitute for a hydroxyl group, including amide (such as acetyl) derivatives), a carboxyl moiety (e.g., carboxylic acid and/or carboxylate salt thereof), and an amino acid moiety.

In another refinement, the binding pair member comprises at least one of a N-acetylglucosamine moiety, a N-acetylgalactosamine moiety, a N-acetylneuraminic acid moiety, a glucose moiety, a galactose moiety, a fucose moiety, a mannose moiety, a rhamnose moiety, a glucuronic acid moiety, a galacturonic acid moiety, an arabinofuranose acid moiety, and a xylose moiety.

In another refinement, the binding pair member comprises a N-acetylglucosamine moiety (e.g., derived from chitosan). In a further refinement, the binding pair member comprises chitosan (e.g., as a biopolymer) and one or more of an oligomeric derivative of chitosan comprising a N-acetylglucosamine moiety, a monomeric N-acetylglucosamine moiety, and a pyrolysis by-product of chitosan.

In another refinement, the binding pair member comprises at least one of a cysteine moiety, a methionine moiety, a glycine moiety, and a lysine moiety (e.g., any moiety from alanine, glycine, isoleucine, leucine, proline, valine, phenylalanine, tryptophan, tyrosine, aspartic acid, glutamic acid, arginine, histidine, lysine, serine, threonine, cysteine, methionine, asparagine, glutamine).

In another refinement, the binding pair member comprises at least one of a carboxylic acid moiety and a carboxylate salt moiety (e.g., a sodium, potassium, or other alkali metal salt).

In another refinement, the binding pair member comprises: a first binding pair member comprising an amino carbohydrate moiety (e.g., an N-acetylglucosamine moiety or other amine or amide carbohydrate derivative); and a second binding pair member comprising at least one of a carbohydrate moiety, a carboxyl moiety, and an amino acid moiety.

In another refinement, the biological target analytes are selected from the group consisting of bacteria (e.g., whole and fragment), viruses (e.g., whole and fragment), proteins (e.g., enzymes or other proteins), and combinations thereof.

In another refinement, the biological target analytes comprise one or more of *Mycobacterium tuberculosis*, *Mycobacterium smegmatis* (and other *Mycobacterium* species), *Escherichia coli* (various strains), *Salmonella enteritidis* (and other *Salmonella* species), *Listeria monocytogenes*, *Vibrio cholera* (and other *Vibrio* species) *Bacillus cereus* (and other *Bacillus* species), Dengue virus, influenza virus, and Newcastle disease virus (e.g., more generally including Gram-positive and/or Gram-negative bacteria).

In another refinement, the binding pair member is covalently bound to the magnetic particle core (e.g., covalent attachment of the binding pair member to the magnetic particle material, such as to an iron or other metal oxide component thereof).

In another refinement, the functionalized magnetic particle composition has a particle size ranging from 50 nm to 1000 nm (e.g., at least 50, 100, 200, 300, 500, 800, or 1000 nm and/or up to 200, 300, 400, 500, 600, 800, 1000, or 2000 nm).

In another refinement, a weight ratio of the magnetic particle core to the biomimetic binding pair member ranges from 4:1 to 1:4 (e.g., up to 10:1, 4:1, 2:1, 1.5:1 and/or up to 1:1.5, 1:2, 1:4, or 1:10).

In another refinement, the functionalized magnetic particle composition is in the form of a particulate powder (e.g., a (dried) free-flowing powder that is generally free from liquids, such as synthesis solvents and/or end-use suspension liquids such as water).

In another refinement, the functionalized magnetic particle composition further comprises (c) water; wherein the water provides a suspending medium for a plurality of functionalized magnetic particles comprising the magnetic particle cores and the biomimetic binding pair member bound thereto in the form of a dispersion (e.g., a stable aqueous dispersion of the functionalized magnetic particles). In a further refinement, the functionalized magnetic particles are present in the suspending medium at a concentration ranging from 0.01 g/L to 100 g/L (e.g., at least 0.01, 0.1, 1, 2, 5, or 10 g/L (or mg/mL) and/or up to 2, 5, 10, 20, 50, or 100 g/L (or mg/mL); such as 1-50 g/L, 2-20 g/L, 3-12 g/L, about 5 g/L, or about 10 g/L).

In another refinement, the functionalized magnetic particle composition is free from specific binding pair members (e.g., specific binding pair members selective to one or more of the biological target analytes to which the non-specific biomimetic binding pair member can bind; such as antibody probes, oligonucleotide probes specific to a target analyte).

In another aspect, the disclosure relates to a method for making a functionalized magnetic particle composition, the method comprising: reacting a magnetic particle precursor with a (biomimetic) binding pair member precursor capable of non-specific binding to a plurality of biological target analytes in a non-aqueous reaction medium under sufficient temperature and pressure to form a functionalized magnetic particle composition according to any of the variously disclosed embodiments and refinements (e.g., functionalized magnetic particle composition comprising: (a) a magnetic particle core; and (b) a (biomimetic) binding pair member bound to an external surface of the magnetic particle core, the binding pair member being capable of non-specific binding to a plurality of biological target analytes). In a refinement, the magnetic particle precursor comprises at least one of an Fe(II) and an Fe(III) salt (e.g., an iron halide salt such as iron chloride, preferably in a hydrate form); and the binding pair member precursor comprises at least one of a carbohydrate, an amino derivative thereof, a carboxyl compound, and an amino acid compound (e.g., a glycan, a glyconjugate).

In another aspect, the disclosure relates to a method for extracting a biological target analyte from a sample, the method comprising: (a) providing a functionalized magnetic particle composition according to any of the variously disclosed embodiments; (b) contacting the functionalized magnetic particle composition with a sample containing or suspected of containing one or more biological target analytes to which the (biomimetic) binding pair member of the functionalized magnetic particle composition is capable of non-specific binding for a time sufficient to bind any biological target analytes in the sample to the functionalized magnetic particle composition, thereby forming a magnetic particle-analyte conjugate (e.g., adding the functionalized magnetic particle composition to the sample medium; adding the functionalized magnetic particle composition and the sample to a third aqueous or other fluid medium); and (c) magnetically separating the magnetic particle-analyte conjugate from the sample (e.g., magnetically immobilizing the magnetic particle-analyte conjugate with an external magnet to the sample, removing/decanting sample supernatant, and then rinsing/washing the remaining sample).

Various refinements of the extraction method are possible.

In a refinement, part (b) comprises contacting the functionalized magnetic particle composition with the sample for a period ranging from 1 minute to 30 minutes before magnetically separating in part (c) (e.g., contacting for at least 1, 2, 3, or 5 minutes and/or up to 5, 10, 15, 20, or 30 minutes to bind/extract any target analyte(s) present in the sample to the functionalize magnetic particles; contacting or incubation for binding/extraction can be performed under mild conditions, such as room temperature (about 20-30° C.)).

In another refinement, the sample comprises a biological material (e.g., a sample of human or other animal tissue or fluid).

In another refinement, the sample is selected from the group consisting of saliva, sputum, urine, blood, cerebrospinal fluid, tracheal swabs, and combinations thereof.

In another refinement, the sample comprises a food item. In a further refinement, the sample is selected from the group consisting of vegetables, fruits, eggs, poultry (chicken), fish, seafood, milk, mayonnaise, components thereof, and combinations thereof.

In another refinement, the extraction method further comprises (d) detecting a specific biological target analyte in the magnetic particle-analyte conjugate (e.g., using any conventional analyte-specific probe or assay, such as with an analyte-specific antibody, oligonucleotide, etc., which is optionally labeled with any suitable detection/reporter moiety, such as a visible reporter, an electrochemical reporter, an enzymatic reporter, etc.).

In another refinement, the extraction method further comprises (d) detecting a non-specific biological target analyte in the magnetic particle-analyte conjugate (e.g., visible observation of a matting/aggregation of the magnetic particle-analyte conjugate, which is indicative of a non-specific bacterial infection in the sample; absence of such matting/aggregation is indicative of a lack of bacterial infection in the sample).

While the disclosed compounds, methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

DETAILED DESCRIPTION

Figure 1:
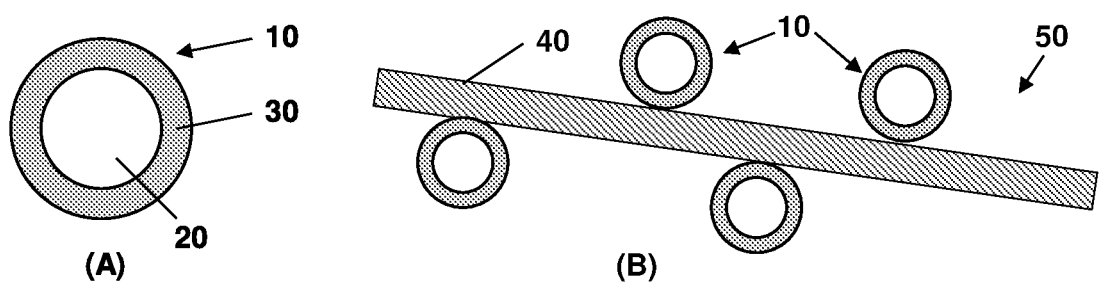
FIG. 1 is a schematic illustrating (A) a functionalized magnetic particle and (B) a functionalized magnetic particle-target analyte conjugate according to the disclosure.

The disclosure relates to a functionalized magnetic particle composition and related method or assay to extract biological target analytes such as bacteria (e.g., *M. tuberculosis, Salmonella, E. coli*, or otherwise) from samples such as clinical, industrial, or environmental samples. In a particular embodiment, functionalized magnetic particles include chitosan-coated iron oxide nanoparticles. The functionalized magnetic particles can be formed by a thermosolvo method. Ferric chloride hexahydrate, anhydrous sodium acetate, and chitosan (e.g., or other source of other biomimetic binding pair members) are added to ethylene glycol. The mixture is stirred for one hour at room temperature and then transferred to a polytetrafluoroethylene (PTFE) cup and placed in a pressure/acid digestion vessel. The reaction is heated to 200° C. for 18 hours and then allowed to cool to room temperature. The solid residue (i.e., functionalized magnetic nanoparticles) is separated, washed, and dried, and is then ready for use. In an illustrative extraction assay, prepared nanoparticles are mixed with a bacteria-containing sample and briefly mixed. The sample can be processed immediately following mixing, in which case a substantial majority of the bacteria present can be captured/conjugated (e.g., at least about 90% in representative test extractions). Capture efficiency can be increased if the test sample is allowed to incubate for a short period (e.g., about 5-10 minutes or more). During mixing and incubation, bacteria hybridize to the chitosan coating of the iron oxide nanoparticles (e.g., or other biomimetic binding pair members bound to the magnetic nanoparticle core). The nanoparticle-bacteria complex can be separated from the supernatant by magnetic separation or centrifugation. The extracted complex can then used with a biosensor to determine if bacteria are present (i.e., the sample extraction method can be used as a front-end sample processing technique for any of a variety of other downstream (biosensor) assays for analyte detection, identification, and/or quantitation, etc.).

The disclosed functionalized magnetic particle composition has several advantages, whether used to extract/detect common target biological analytes such as *M. tuberculosis, Salmonella, E. coli*, or otherwise. The disclosed composition is low-cost, having an estimated material cost per assay of $0.009. The disclosed extraction method is rapid, having a completed extraction in about 15-30 minutes (e.g., including sample preparation, incubation (if desired), magnetic particle separation, etc.). The disclosed extraction method can be instrument-free, using only a simple magnet for an extraction assay, which is very much amenable to low-resource settings. The disclosed composition can be antibody-free, with the extraction assay not requiring antibodies for target-specific binding and detection (although such antibodies can be included in some embodiments if desired), thus reducing costs and permitting composition storage at room temperature. The disclosed composition has global applicability in resource-limited settings. Because it does not require refrigeration and it is inexpensive, the disclosed composition facilitates the diagnosis of tuberculosis and other infectious agents around the world. At the moment, 2 billion people globally are infected with tuberculosis, with about 10 million new cases occurring each year and with about 1.3-1.5 million dying from the disease each year. Related technologies include smear microscopy which was discovered in 1880 and is still the main diagnostic technique globally. The most recent technology endorsed by the World Health Organization (WHO) is the GENEXPERT technology, which is a DNA-based detection system that is very expensive (at $30 per test) and requires expensive PCR-based instrumentation. The disclosed composition in some embodiments (e.g., chitosan-coated magnetic particles) includes glucosamine units on the iron oxide magnetic particles, which allows for substrate-cell adhesion. The disclosed composition can further utilize pattern recognition receptors (PRR) in analyte extraction/binding. Pattern recognition receptors are proteins expressed by cells of the innate immune system to identify pathogen-associated molecular patterns (PAMP) which are associated with microbial pathogens or cellular stress, as well as damage-associated molecular patterns (DAMP) which are associated with cell components released during cell damage. The microbe-specific molecules that are recognized by a given PRR are called pathogen-associated molecular patterns and include bacterial carbohydrates (such as lipopolysaccharide or LPS and mannose), nucleic acids, bacterial peptides, peptidoglycans, and lipoteichoic acids, N-formylmethionine, lipoproteins, and fungal glucans.

Functionalized Magnetic Particle Composition

As illustrated in FIG. 1, a functionalized magnetic particle 10 composition according to the disclosure includes a magnetic particle core 20 and a binding pair member 30 bound to the magnetic particle core 20 (FIG. 1, panel A). The magnetic particle core 20 (e.g., an iron oxide or otherwise as described below) is generally a nano- or micro-scale particle having a roughly spherical shape. The binding pair member 30 (e.g., a glycan or component or derivative thereof or otherwise as described below) is suitably a biomimetic, non-specific binding ligand and is generally capable of non-specific binding to one or more biological target analytes 40 (FIG. 1, panel B showing a functionalized magnetic particle-target analyte conjugate 50 including a target analyte 40 such as a bacterium bound to multiple functionalized magnetic particles 10). The biomimetic binding pair member 30 is bound to an external or outer surface of the magnetic particle core 20, although some binding pair member 30 can additionally be interspersed throughout the body of the magnetic particle core 20 such that the binding capability to the target analytes results from the binding pair members 30 that are at or on the outer surface of the magnetic particle core 20. Additionally, the binding pair member 30 can be interspersed within magnetic nanoparticle 20 clusters (e.g., also at external and/or internal surfaces thereof).

The magnetic particle core according to the disclosure is not particularly limited and generally includes any nano- or micro-sized magnetic particles (e.g., about 1 nm to about 1000 nm or 2000 nm) that can be magnetized with an external magnetic/electrical field. More generally, the magnetic particle core can have a particle size ranging from 1 nm to 2000 nm (e.g., at least 1, 2, 10, 20, 50, 100, 200, 300, 500, 800, or 1000 nm and/or up to 200, 300, 400, 500, 600, 800, 1000, or 2000 nm), where the particle size ranges can represent a range for the average particle size (e.g., a number-, volume-, or weight-based average particle size) and/or the particle size ranges can represent the span of the distribution (e.g., such as for all or substantially all particles; such as between the 10% and 90% sizes of the cumulative size distribution). The magnetic particles more particularly include superparamagnetic particles, which particles can be easily magnetized with an external magnetic field (e.g., to facilitate separation or concentration of the particles from the bulk of a sample medium) and then redispersed immediately once the magnet is removed (e.g., in a new (concentrated) sample medium). Thus, the magnetic particles are generally separable from solution with a conventional magnet. Suitable magnetic particles mainly include nano-sized iron oxide particles, in particular $Fe_3O_4$ (magnetite) or $\gamma$-$Fe_2O_3$; (maghemite). Such magnetic particles can be prepared by superparamagnetic iron oxide by precipitation of ferric and ferrous salts in the presence of sodium hydroxide and subsequent washing with water.

More generally, the magnetic particle core and corresponding magnetic particles can include a ferrimagnetic or ferromagnetic material (e.g., iron-containing particles providing electrical conduction or resistance). Suitable magnetic particles include iron-containing magnetic metal oxides, for example those including iron either as Fe(II), Fe(III), or a mixture of Fe(II)/Fe(III) (e.g., iron in a +2 and/or +3 oxidation state). Non-limiting examples of such oxides include an iron(II,III) oxide ($Fe_3O_4$; magnetite), an iron(II) oxide (FeO), or an iron(III) oxide ($\gamma$-$Fe_2O_3$; maghemite). The magnetic nanoparticles can also be a mixed metal oxide of the type $M1_xM2_{3-x}O_4$, wherein M1 represents a divalent metal ion and M2 represents a trivalent metal ion. For example, the magnetic nanoparticles may be magnetic ferrites of the formula $M1Fe_2O_4$, wherein M1 represents a divalent ion selected from Mn, Co, Ni, Cu, Zn, or Ba, pure or in admixture with each other or in admixture with ferrous ions. Other metal oxides include aluminum oxide, chromium oxide, copper oxide, manganese oxide, lead oxide, tin oxide, titanium oxide, zinc oxide and zirconium oxide, and suitable metals include Fe, Cr, Ni or magnetic alloys.

The binding pair member suitably is a biomimetic, non-specific binding ligand and is generally capable of non-specific binding to one or more biological target analytes. The binding pair member can include one or more glycans or glycoconjugates (e.g., glycoproteins, glycopeptides, peptidoglycans, glycolipids, glyco-oligonucleotides, glycosides, lipopolysaccharides) as well as components or fragments thereof (e.g., including one or more saccharide, protein, peptide, nucleotide, and/or lipid components from the glycans or glycoconjugates). Glycans generally consist of O-glycosidic linkages of monosaccharides, and glycoconjugates generally include a carbohydrate or polysaccharide portion covalently bonded to one or more other saccharide, protein, peptide, nucleotide, and/or lipid portions. Glycans, glycoconjugates, and components or fragments thereof in a natural setting can be involved in cell-cell interactions and recognition, and their inclusion as a binding pair member in the functionalized magnetic particle can provide corresponding biomimetic, non-specific binding capability for one or more biological target analytes (e.g., cell components thereof) to the functionalized magnetic particle. More generally, the binding pair member can function as a biomimetic pattern recognition receptor to distinguish pathogen-associated molecular patterns (e.g., lipopolysaccharide, mannose, peptidoglycans, lipoproteins, etc.) and facilitate non-specific binding to one or more biological target analytes. The biomimetic binding pair member is generally not capable of specific binding to a specific target analyte and does not typically include antibodies or oligonucleotides specific to a target analyte, for example.

In some embodiments, the binding pair member includes at least one of a carbohydrate moiety, an amino derivative thereof (e.g., amino sugar moiety or other carbohydrate/saccharide including an amine group substitute for a hydroxyl group, including amide (such as acetyl) derivatives), a carboxyl moiety (e.g., carboxylic acid and/or carboxylate salt thereof), and an amino acid moiety. Such binding pair members can be components of or otherwise derived from one or more glycans or glycoconjugates, The binding pair members can include monomeric, oligomeric (such as 2-10 residues), or polymeric forms of the various moieties, such as monosaccharides, disaccharides, oligosaccharides, and polysaccharides whether or not substituted with an amino group, as well as single amino acids, oligopeptides, and polypeptides. Examples of suitable binding pair members in the form of a carbohydrate moiety or an amino derivative thereof (e.g., as glycan components or otherwise) include one or more of a N-acetylglucosamine moiety, a N-acetylgalactosamine moiety, a N-acetylneuraminic acid moiety, a glucose moiety, a galactose moiety, a fucose moiety, a mannose moiety, a rhamnose moiety, a glucuronic acid moiety, a galacturonic acid moiety, an arabinofuranose acid moiety, and a xylose moiety. Examples of suitable binding pair members in the form of an amino acid moiety include one or more moieties from alanine, glycine, isoleucine, leucine, proline, valine, phenylalanine, tryptophan, tyrosine, aspartic acid, glutamic acid, arginine, histidine, lysine, serine, threonine, cysteine, methionine, asparagine, and glutamine (e.g., any desired amino acid). Examples of suitable binding pair members in the form of a carboxyl moiety include a carboxylic acid moiety and a carboxylate salt moiety (e.g., a sodium, potassium, or other alkali metal salt), such as in the form of a (meth)acrylic polymer coated on the magnetic particle core.

In a particular embodiment, the binding pair member comprises a N-acetylglucosamine moiety, for example as derived from chitosan. Chitosan is a linear polysaccharide composed of acetylated (N-acetyl-D-glucosamine) and deacetylated (β-(1→4)-linked D-glucosamine)glucosamine units. The amino sugar N-acetyl-D-glucosamine (GlcNAc or NAG) plays structural roles at a cell surface, being a component of bacterial and other cell wall peptidoglycans, fungal cell wall chitin, extracellular matrix of animal cells, and cell signaling. Chitosan also contributes to biofilm formation and substrate/intercellular adhesion. Chitosan can be incorporated into the functionalized magnetic particle as a binding pair member in one or more forms, including its original biopolymer/polymeric form (e.g., including both acetylated NAG units and deacetylated units), cleaved oligomeric units from the original biopolymer (e.g., including one or both of acetylated NAG units and deacetylated units, such as with 2 to 10, 20, or 50 monomeric units in the oligomer), cleaved monomeric units from the original biopolymer (e.g., including both acetylated NAG units and deacetylated units separately), and pyrolysis by-products of chitosan (e.g., including carbon and/or carbon nitride (aminated carbon)). Incorporation of chitosan into the functionalized magnetic particle in several different forms can result from a reaction process (e.g., a thermosolvo reaction process as illustrated in Example 1 below) to form the functionalized magnetic particle composition. Such reaction processes can be performed at about 200° C. for the synthesis of magnetic particle cores in the presence of a binding pair member source (e.g., chitosan biopolymer) to form the functionalized magnetic particle composition. Chitosan begins to degrade (e.g., depolymerize and/or pyrolyze) at about 200° C., thus resulting in incorporation of one or more of the original chitosan and foregoing degradation products into the functionalized magnetic particle composition. In addition to being a component of or derived from chitosan, N-acetylglucosamine can be incorporated as a monomer (e.g., from any suitable commercial source) as the binding pair member.

In some embodiments, the functionalized magnetic particle can include two or more different binding pair members, for example from the same or different general classes above (e.g., carbohydrate moiety, amino derivative thereof, carboxyl moiety, amino acid moiety). For example, in an embodiment, the functionalized magnetic particle can include a first binding pair member with an amino carbohydrate moiety (e.g., an N-acetylglucosamine moiety or other amine or amide carbohydrate derivative) and a second binding pair member with at least one of a carbohydrate moiety, a carboxyl moiety, and an amino acid moiety. Multiple different binding pair members can provide binding capability to a broader selection of biological target analytes. The inclusion of a select binding pair member can further improve size control and dispersion stability of the functionalized magnetic particle composition. For example, an amino carbohydrate moiety (such as an N-acetylglucosamine moiety or otherwise) can induce small particle size (about 200 nm or 300 nm to 500 nm or 600 nm with a narrow distribution) and can provide some hydrophilic surface groups to provide a stable, easily re-dispersible dispersion in water. The small size, stable dispersion, and binding capability of the functionalized magnetic particle composition makes it very fast to hybridize, capture, and magnetically separate various target analytes from a sample matrix.

A wide variety of biological target analytes may be bound/extracted by the functionalized magnetic particle composition. Suitable biological target analytes can include one or more bacteria (e.g., whole and fragment), one or more viruses (e.g., whole and fragment), and/or one or more proteins (e.g., enzymes or other proteins). In some embodiments, the binding pair member can be selective for different classes of target analytes, such being capable of non-specific binding to multiple bacteria, but not generally to viruses or proteins (e.g., alternatively able to bind viruses but not bacteria or proteins, able to bind proteins but not bacteria or viruses, etc.). In further embodiments, the binding pair member can be selective within a class of target analytes, such as capable of non-specific binding to multiple types of bacteria, but not other types of bacteria (e.g., and likewise for virus and/or protein targets). Examples of specific biological target analytes of interest include one or more of *Mycobacterium tuberculosis*, *Mycobacterium smegmatis* (and other *Mycobacterium* species), *Escherichia coli* (various strains), *Salmonella enteritidis* (and other *Salmonella* species), *Listeria monocytogenes*, *Vibrio cholera* (and other *Vibrio* species) *Bacillus cereus* (and other *Bacillus* species), Dengue virus, influenza virus, and Newcastle disease virus. In some embodiments, the biological target analytes can include more generally Gram-positive and/or Gram-negative bacteria. In some embodiments, the functionalized magnetic particle composition can be used to extract fungi, plant diseases, and/or animal diseases from a plant or animal biological sample.

Figure 2:
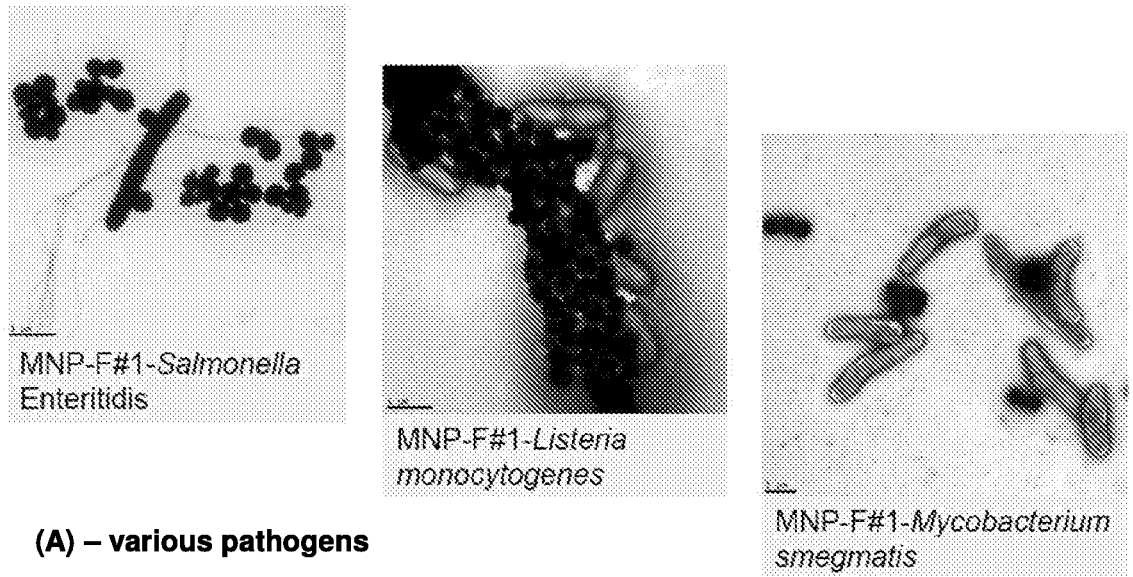
FIG. 2 includes transmission emission microscope (TEM) images of functionalized magnetic particle-target analyte conjugates for chitosan-coated magnetic nanoparticles ("MNP-F #1"), cysteine-coated magnetic nanoparticles ("MNP-F #2"), and carboxylate-coated magnetic nanoparticles ("MNP-F #3") with bacterial target analytes including *Listeria monocytogenes* (panels A and B), *Salmonella enteritidis* (panels A and C), and *Mycobacterium smegmatis* (panels A and D).
Figure 2:
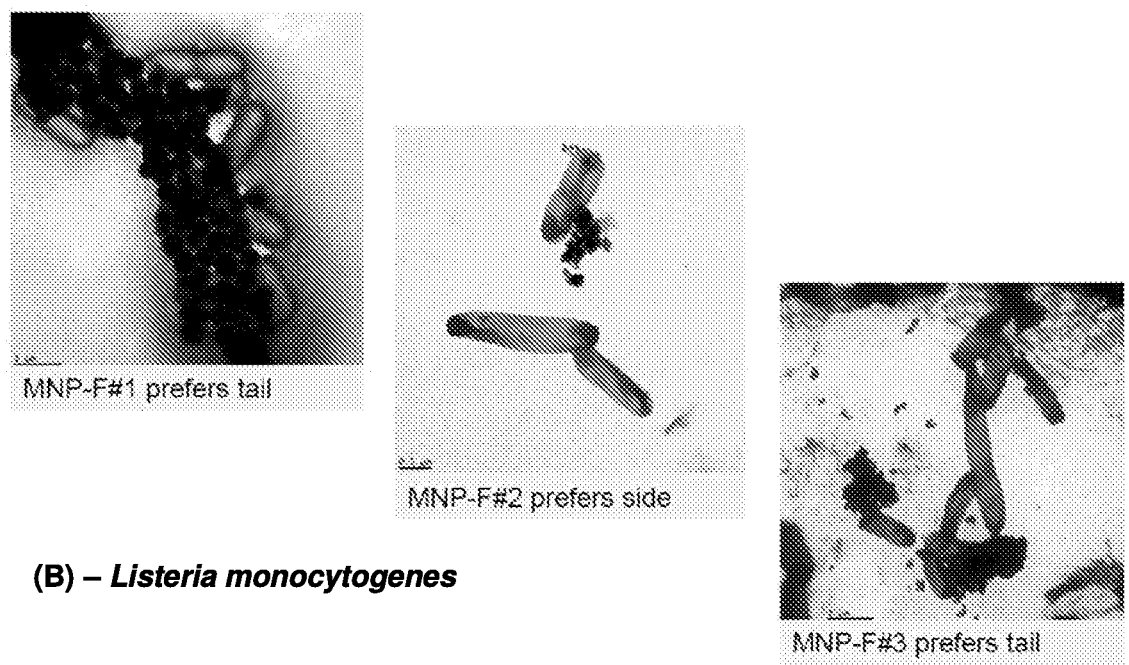
Figure 2:
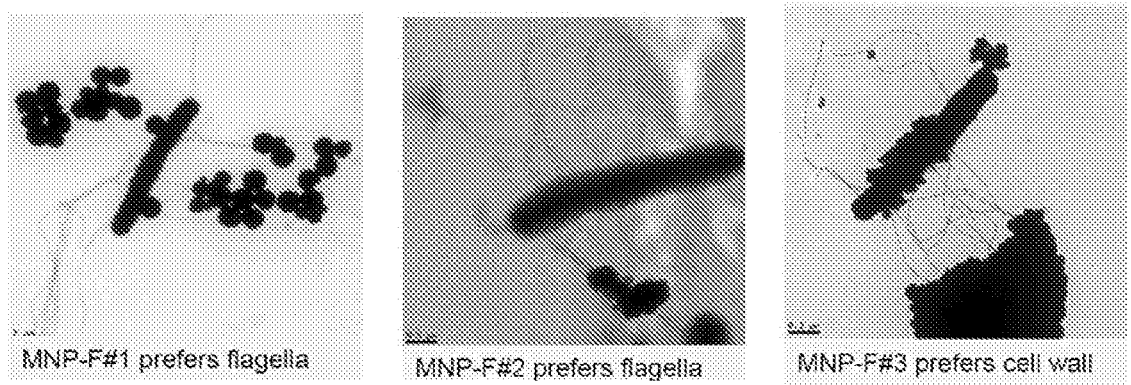
Figure 2:
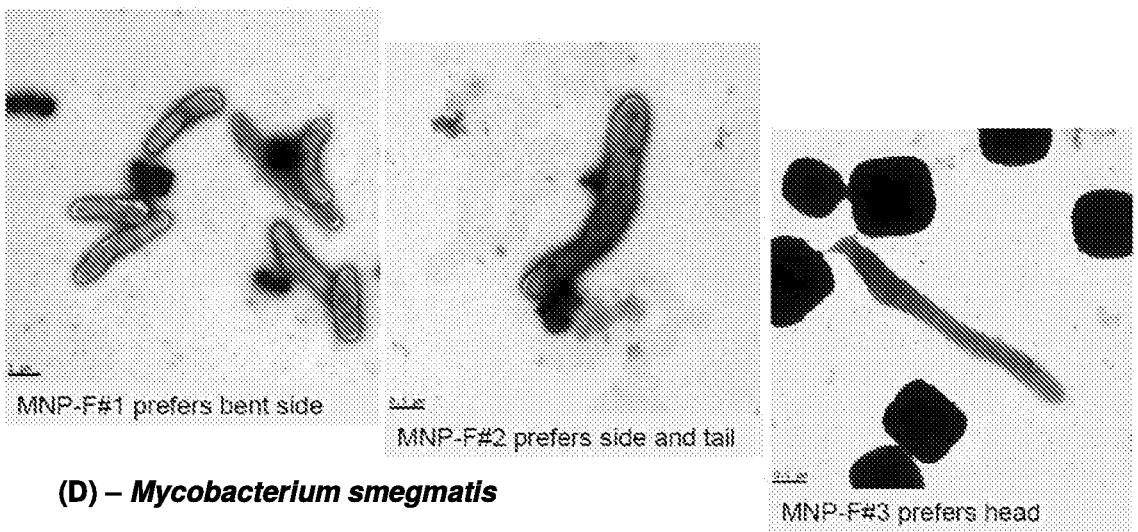

FIG. 2 illustrates the ability of the disclosed functionalized magnetic particle composition to non-specifically bind to a wide variety and plurality of biological target analytes. FIG. 2 includes transmission emission microscope (TEM) images of functionalized magnetic particle-target analyte conjugates for chitosan-coated magnetic nanoparticles ("MNP-F #1"), cysteine-coated magnetic nanoparticles ("MNP-F #2"), and carboxylate-coated magnetic nanoparticles ("MNP-F #3") with bacterial target analytes including *Listeria monocytogenes* (panels A and B), *Salmonella enteritidis* (panels A and C), and *Mycobacterium smegmatis* (panels A and D). As illustrated, a variety of binding morphologies are possible, including binding to the tail, side, and/or head portion of a given bacterial target analyte for a given functionalized magnetic particle/binding pair member.

Suitably, the binding pair member is covalently bound to the magnetic particle core, for example including covalent attachment of the binding pair member to the magnetic particle material, such as an iron oxide component thereof. Typically, covalent binding can result from amino group-metal and/or hydroxyl group-metal covalent bonds, for example including —NH—Fe and —O—Fe bonds (e.g., resulting from reaction with —NH$_2$ and —OH groups present from chitosan with Fe present from an iron oxide magnetic particle core). In addition to chitosan, binding pair members more generally including NAG, carbohydrates, amino acids, etc. include amino groups and/or hydroxy groups, and they can similarly form covalent amino group-metal and/or hydroxyl group-metal bonds to the magnetic particle core. Adsorption of the binding pair member on the magnetic particle core is possible, but it is generally not the exclusive means for attachment. In some cases, covalent attachment is the exclusive means for attachment.

The particle size of the functionalized magnetic particle composition is not particularly limited. In some embodiments, the functionalized magnetic particle composition has a particle size ranging from 50 nm to 1000 nm. In other embodiments, the functionalized magnetic particle composition can have a particle size at least 50, 100, 200, 300, 500, 800, or 1000 nm and/or up to 200, 300, 400, 500, 600, 800, 1000, 2000, or 5000 nm. The particle size ranges can represent a range for the average particle size, such as a number-, volume-, or weight-based average particle size. Similarly, the particle size ranges can represent the span of the distribution, such as for all or substantially all particles, such as between the 10% and 90% sizes of the cumulative size distribution. Suitably, magnetic attraction between adjacent magnetic particle cores is weak enough such that van der Waals forces between the binding pair members are sufficient to prevent magnetic clumping or agglomeration of the corresponding functionalized magnetic particle composition when in the form of an aqueous dispersion. A corresponding nanoscale size of the functionalized magnetic particle composition (e.g., at least 100, 200, or 300 nm and/or up to 200, 300, 400, or 500 nm) is suitably selected to provide a colloidal suspension through Brownian motion.

The relative amounts of the magnetic particle core and the biomimetic binding pair member in the functionalized magnetic particle composition are not particularly limited. In some embodiments, a weight ratio of the magnetic particle core to the biomimetic binding pair member ranges from 4:1 to 1:4 (e.g., up to 10:1, 4:1, 2:1, 1.5:1 and/or up to 1:1.5, 1:2, 1:4, or 1:10). In other embodiments, the magnetic particle core and/or the biomimetic binding pair member independently can be present in the functionalized magnetic particle composition in amounts of at least 10, 20, 30, 40 or 50 wt. % and/or up to 50, 60, 70, 80 or 90 wt. % (e.g., about 30 or 40 wt. % to about 60 or 70 wt. %).

The specific form of the functionalized magnetic particle composition is not particularly limited. In some embodiments, the functionalized magnetic particle composition is in the form of a particulate powder, for example including a (dried) free-flowing powder that is generally free from liquids, such as synthesis solvents and/or end-use suspension liquids such as water. In other embodiments, the functionalized magnetic particle composition further includes water (e.g., distilled and/or deionized water) and is in the form of an aqueous suspension. The water provides a suspending medium for a plurality of functionalized magnetic particles in the form of a dispersion (e.g., a stable aqueous dispersion of the functionalized magnetic particles). The aqueous medium can include further components, such as buffer components for phosphate-buffered saline or otherwise. The functionalized magnetic particles suitably are present in the suspending medium at a concentration ranging from 0.01 g/L to 100 g/L (e.g., at least 0.01, 0.1, 1, 2, 5, or 10 g/L (or mg/mL) and/or up to 2, 5, 10, 20, 50, or 100 g/L (or mg/mL). Typical working concentrations that also form stable dispersions include 1 to 50 g/L, 2 to 20 g/L, 3 to 12 g/L, about 5 g/L, or about 10 g/L.

As described above, the functionalized magnetic particle composition includes a non-specific biomimetic binding pair member for one or more biological target analytes and need not necessarily include a specific binding pair member for one or more same or different biological target analytes. In some embodiments, the functionalized magnetic particle composition is free from specific binding pair members (e.g., specific binding pair members selective to one or more of the biological target analytes to which the non-specific biomimetic binding pair member can bind), such as antibody probes and/or oligonucleotide probes specific to a target analyte. In other embodiments, the functionalized magnetic particle composition can include a specific binding pair member for a desired target analyte. In such cases, the biomimetic binding pair member can serve an additional or alternative function, such as providing a means for particle size control and suspension stability, a reporter/label moiety, etc.

Methods

The disclosed functionalized magnetic particle composition can be formed using any suitable method, for example including a one-pot solvothermal synthesis. Suitably, a magnetic particle precursor and a binding pair member precursor capable of non-specific binding to a plurality of biological target analytes are reacted in a non-aqueous reaction medium under sufficient temperature and pressure to form a functionalized magnetic particle composition according to the disclosure. The magnetic particle precursor can include a metal salt of a corresponding magnetic metal as generally described above, for example including at least one of an Fe(II) and an Fe(III) salt (e.g., an iron halide salt such as iron chloride, preferably in a hydrate form). The binding pair member precursor can include one or more of a glycan, a glyconjugate, and a component thereof as generally describe above. In various embodiments, the binding pair member precursor includes at least one of a carbohydrate, an amino derivative thereof, a carboxyl compound, and an amino acid compound as generally described above (e.g., for the corresponding moieties as incorporated into the functionalized magnetic particle). The reaction can be performed in any desired solvent, for example a polar organic solvent (e.g., ethylene glycol, other alcohols or diols), and can further include an initiator for metal (e.g., iron) oxide nucleation and magnetic particle core formation (e.g., sodium acetate).

The disclosed functionalized magnetic particle composition can be used to extract a biological target analyte from a sample. The functionalized magnetic particle composition is contacted with a sample containing or suspected of containing one or more biological target analytes to which the (biomimetic) binding pair member of the functionalized magnetic particle composition is capable of non-specific binding for a time sufficient to bind any biological target analytes in the sample to the functionalized magnetic particle composition. After a sufficient binding time, a magnetic particle-analyte conjugate is formed in the sample medium. In various embodiments, contacting the functionalized magnetic particle composition with the sample can be performed by adding the functionalized magnetic particle composition to the sample medium, adding the functionalized magnetic particle composition and the sample to a third aqueous or other fluid medium, etc. In various embodiments, the functionalized magnetic particle composition is contacted with the sample for a period ranging from 1 minute to 30 minutes before subsequent magnetic separation (e.g., contacting for at least 1, 2, 3, or 5 minutes and/or up to 5, 10, 15, 20, or 30 minutes to bind/extract any target analyte(s) present in the sample to the functionalize magnetic particles). Contacting or incubation for binding/extraction can be performed under mild conditions, such as room temperature (e.g., about 20-30° C.). The magnetic particle-analyte conjugate is then magnetically separated from the sample. For example, magnetic separation can include magnetically immobilizing the magnetic particle-analyte conjugate with an external magnet to the sample, removing/decanting sample supernatant, and then rinsing/washing the remaining sample with a suitable wash fluid (e.g., PBS) to remove any remaining sample matrix, and optionally re-suspending the magnetic particle-analyte conjugate in the wash fluid.

The sample to be tested and extracted is not particularly limited and can include any of a variety of biological materials, food products, environmental samples (e.g., environmental water or soil), surface swabs testing for contamination, etc. For example, the sample can be a biological material such as a sample of human or other animal tissue or fluid, for example including saliva, sputum, urine, blood, cerebrospinal fluid, tracheal swabs, etc. In other embodiments, the sample can be a food item, such as one or more of vegetables, fruits, eggs, poultry (chicken), fish, seafood, milk, mayonnaise, spinach, and components thereof. Food items suitably can be ground, shredded, otherwise reduced in size, etc. and/or added to a fluid sample medium to which the functionalized magnetic particle composition is also added to form the magnetic particle-analyte conjugate.

In various embodiments the method for extracting a biological target analyte from a sample can be extended to a method of detection as well, such as where the extraction method is used as a front end processing method for any desired (conventional) detection method to identify and/or quantify particular target analytes in the original sample. For example, the method can be extended by detecting a specific biological target analyte in the magnetic particle-analyte conjugate extract, such as by using any conventional analyte-specific probe or assay (e.g., with an analyte-specific antibody, oligonucleotide, etc.), which probe is optionally labeled with any suitable detection/reporter moiety, such as a visible reporter, an electrochemical reporter, an enzymatic reporter, etc. Alternatively or additionally, the method can be extended by detecting a non-specific biological target analyte in the magnetic particle-analyte conjugate. For example, visible observation of a matting/aggregation of the magnetic particle-analyte conjugate in the extracted sample can be is indicative of a non-specific bacterial infection in the sample (i.e., and correspondingly in a human patient, animal, or other organism from which the sample is obtained). Matting of the magnetic particle-analyte conjugate can be observed as a relatively large surface area sheet or thin aggregate of the conjugate, which forms or accumulates at or near the surface of a sample container in which the conjugate is formed or is present. Namely, the presence of such matting/aggregation of the magnetic particle-analyte conjugate need not generally identify the particular pathogen causing the infection, but nonetheless indicates the presence of some type of bacterial infection (e.g., as a non-specific positive/negative screening for infection without identification of the specific infection). Similarly, the absence of such matting/aggregation of the magnetic particle-analyte conjugate in the extracted sample is indicative of a lack of bacterial infection in the sample. Of course, if a non-specific biological target analyte is detected (e.g., by visible observation of matting/aggregation or otherwise), the magnetic particle-analyte conjugate extract can be further tested by one or more conventional methods to identify the specific biological target analyte as described above.

EXAMPLES

The examples illustrate the disclosed compositions and processes, but are not intended to limit the scope of any claims thereto.

Example 1—Synthesis of Chitosan-Coated Magnetic Nanoparticles

The following materials are used to form chitosan-coated magnetic nanoparticles as a functionalized magnetic particle composition according to the disclosure: (a) Ferric chloride hexahydrate ($FeCl_3 \cdot 6H_2O$, FW: 270.30), (b) Chitosan, low molecular weight, (c) Sodium acetate (anhydrous, $NaCH_3COO$, FW: 82.03), (d) Ethylene glycol, (e) Deionized water, and (f) Pure Ethanol (200 proof).

The chitosan-coated magnetic nanoparticles are formed according to the following procedure: (1) Use a 200-mL pressure/acid digestion vessel as a reaction vessel, which vessel contains a PTFE-lined cup. (2) In a 150-mL beaker, dissolve 2.0 g of ferric chloride hexahydrate ($FeCl_3 \cdot 6H_2O$) in 75 mL of ethylene glycol with magnetic stirring until solution is clear, generally about 10 minutes. Magnetic stirring is done by adding a small magnetic bar inside the beaker and placing the beaker on a stirring plate set at 350 rpm. (3) Then add 12.0 g of anhydrous sodium acetate and 0.8 g of chitosan to the beaker and stir the mixture vigorously (750-1,000 rpm on a stirring plate) for about 1 hr at room temperature (about 20-25° C.) until a homogeneous brown solution is observed. (4) Immediately remove the magnetic bar and quickly pour the brown solution to the 200-mL PTFE-lined cup (e.g., such that quick pouring will allow majority of the undissolved chitosan to transfer). (5) Insert the PTFE-lined cup into the pressure/acid digestion vessel and seal the pressure vessel. (6) Place the pressure vessel inside the oven. Turn on the oven and heat to 200° C. Keep the vessel in the oven for 8 hr. (7) After the reaction, switch off the oven and let the vessel completely cool to room temperature (e.g., overnight or about 8 hr). Complete cooling will allow the solution to reach equilibrium and improve hydrophilicity. (8) Using a 25-ml pipette attached to an electric pipette, remove about 50 ml of the solvent (above the solution) and discard as waste. Then transfer the remaining solution to a 50-mL tube. (9) Wash the chitosan-coated magnetic (Chi-$Fe_3O_4$) nanoparticles (MNPs) initially with 20-50 mL distilled water, and then sequentially with 20 mL distilled water followed by 20 mL of pure ethanol at least four times (washing is done by using a magnet to remove the supernatant). (10) Transfer the MNPs to a 50-mL beaker. Additional pure ethanol may be used to complete the transfer. Remove supernatant using a magnet. (11) Air-dry the MNPs in the beaker for 3-4 hr (e.g., in a fume hood or on a laboratory bench). (12) After drying, scrape/recover the dried MNPs and store in a clean dark glass vial.

For the synthesis of mannose-, cysteine-, glycine-, lysine-, or mannan-coated magnetic nanoparticles, follow the foregoing procedure, but replace chitosan with D-mannose, L-cysteine, glycine, lysine, or glucomannan, respectively.

Example 2—Synthesis of Chitosan/Cysteine-Coated Magnetic Nanoparticles

The materials of Example 1, further including L-cysteine, are used to form chitosan/cysteine-coated magnetic nanoparticles as a functionalized magnetic particle composition according to the disclosure.

The chitosan/cysteine-coated magnetic nanoparticles are formed according to the following procedure: (1) Use a 200-mL pressure/acid digestion vessel as a reaction vessel, which vessel contains a PTFE-lined cup. (2) In a 150-mL beaker, dissolve 2.0 g of ferric chloride hexahydrate ($FeCl_3 \cdot 6H_2O$) in 75 mL of ethylene glycol with magnetic stirring until solution is clear, generally about 10 minutes. Magnetic stirring is done by adding a small magnetic bar inside the beaker and placing the beaker on a stirring plate set at 350 rpm. (3) Then add 12.0 g of anhydrous sodium acetate, 0.8 g of chitosan, and 0.2 g of L-cysteine to the beaker and stir the mixture vigorously (750-1,000 rpm on a stirring plate) for about 1 hr at room temperature (about 20-25° C.) until a homogeneous dark green solution is observed. (4) Immediately remove the magnetic bar and quickly pour the dark green solution to the 200-mL PTFE-lined cup (e.g., such that quick pouring will allow majority of the undissolved chitosan to transfer). Follow steps (5)-(12) from Example 1 to complete the synthesis.

For the synthesis of chitosan/mannose-coated magnetic nanoparticles or chitosan/methionine-coated magnetic nanoparticles, follow the foregoing procedure, but replace L-cysteine with D-mannose or L-methionine, respectively.

Example 3—Synthesis of Chitosan/Carboxyl-Coated Magnetic Nanoparticles

The materials of Example 1, further including sodium acrylate, are used to form chitosan/carboxyl-coated magnetic nanoparticles as a functionalized magnetic particle composition according to the disclosure.

The chitosan/carboxyl-coated magnetic nanoparticles are formed according to the following procedure: (1) Use a 200-mL pressure/acid digestion vessel as a reaction vessel, which vessel contains a PTFE-lined cup. (2) In a 150-mL beaker, dissolve 2.0 g of ferric chloride hexahydrate ($FeCl_3 \cdot 6H_2O$) in 75 mL of ethylene glycol with magnetic stirring until solution is clear, generally about 10 minutes. Magnetic stirring is done by adding a small magnetic bar inside the beaker and placing the beaker on a stirring plate set at 350 rpm. (3) Then add 12.0 g of anhydrous sodium acetate, 0.8 g of chitosan, and 1.0 g of sodium acrylate to the beaker and stir the mixture vigorously (750-1,000 rpm on a stirring plate) for about 1 hr at room temperature (about 20-25° C.) until a homogeneous brown solution is observed. (4) Immediately remove the magnetic bar and quickly pour the brown solution to the 200-mL PTFE-lined cup (e.g., such that quick pouring will allow majority of the undissolved chitosan to transfer). Follow steps (5)-(12) from Example 1 to complete the synthesis.

Example 4—Pathogen Extraction and Visual/Optical Detection by MNP Matting

The following materials are used to extract biological target analytes using a functionalized magnetic nanoparticle (MNP) composition according to the disclosure: (a) 0.01 M PBS (phosphate-buffered saline; pH 7.2), and (b) functionalized magnetic nanoparticle (MNP) composition according to the disclosure as an aqueous dispersion at a concentration of 5 mg MNP/mL of dispersion, for example chitosan-coated magnetic nanoparticles according to Example 1 above as well as other MNP compositions according to the Examples 1-3 or the general disclosure. The following procedures can be used to test saliva samples, sputum samples, urine samples, and other biological fluid/material samples for biological target analyte extraction.

Figure 3:
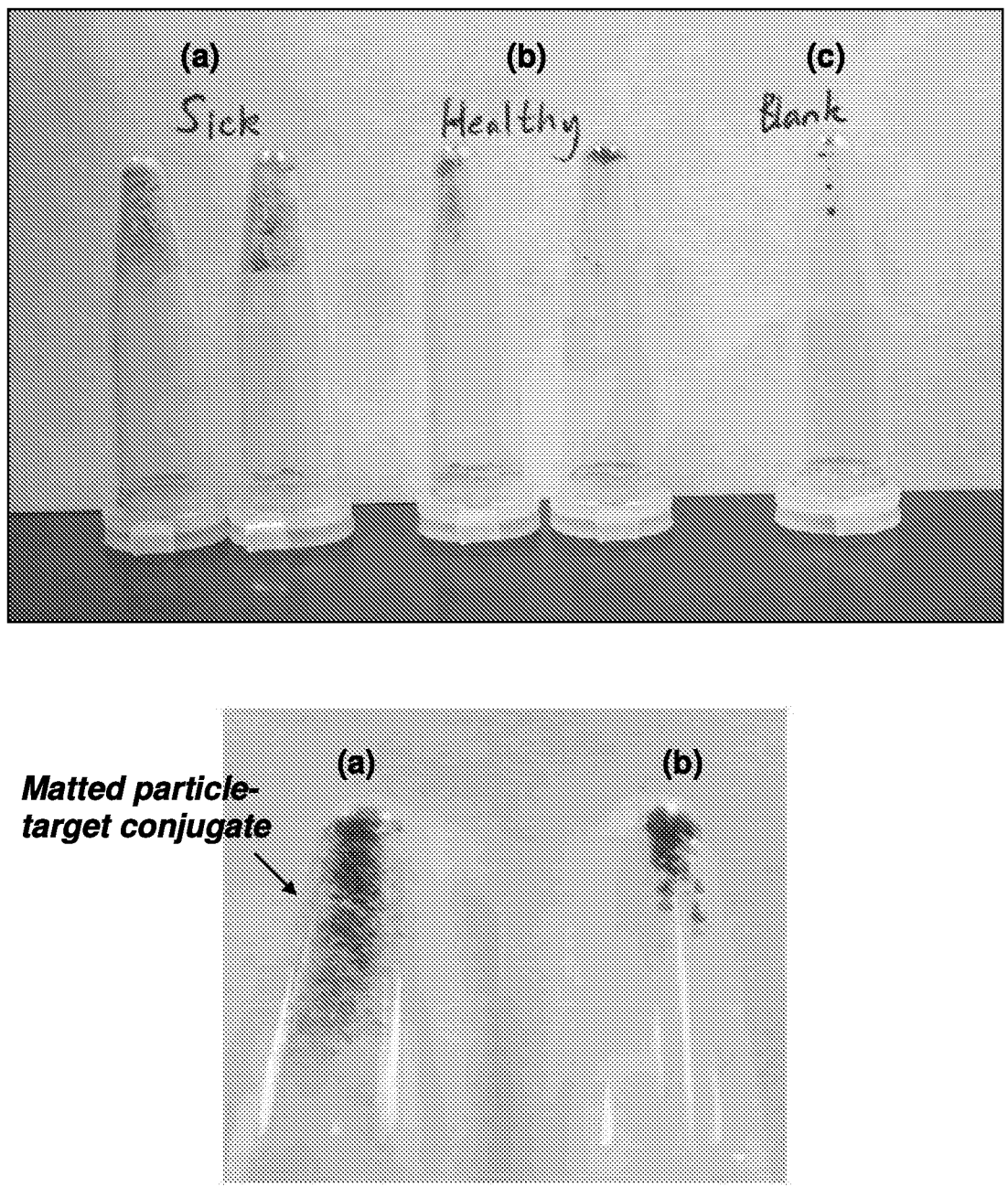
FIG. 3 includes photographs illustrating samples in which (a) functionalized magnetic particle-target analyte conjugate matting is observed, suggesting that a patient is sick (e.g., currently infected; showing symptoms of illness or about to show symptoms soon), (b) functionalized magnetic particle-target analyte conjugate matting is not observed, suggesting that a patient is healthy (e.g., currently not infected; no symptoms of illness or recovering from previous illness), and (c) functionalized magnetic particle-target analyte conjugate matting is not observed in a blank/control sample.

The following extraction procedure is designed for a saliva sample, but can be used for other samples such as urine samples and other fluid/material samples, biological or otherwise: (1) For each sample, pre-fill a microcentrifuge sample tube with 90 µL 0.01M PBS. For a corresponding reference tube, pre-fill with 100 µL PBS. (2) Pipette mix 5× the saliva sample from its original container and draw up 10 µL, making sure not to draw up bubbles. Add the saliva to the sample tube and pipette mix 5×. (3) Add 5 µL of 5 mg/mL MNP to the sample tube. Tap/flick the tube using the front of a finger (not the fingernail) 20× to mix. (4) Let sample stand for 5 min. (5) Tap/flick the tube 20× to mix and flick downward to collect all of the fluid to the bottom of the tube. (6) Open the tubes, place in a magnetic separator, and let stand for 1 min. (7) Use a pipette to slowly remove the supernatant. Keep the tip at the front end of the tube (away from the MNP) and stay barely below the fluid surface while drawing the supernatant. (8) Remove the tubes from the magnetic separator and close them. Observe the area covered by the MNP mat to detect/diagnose whether one or more biological target analytes were present in the original sample based on formation of a visible nanoparticle mat (e.g., analytes present) or absence thereof (e.g., analytes not present). (9) If desired as a means for confirmation and/or biological target analyte identification, use 10 µL of the matted sample to perform a second assay such as smear microscopy or DNA detection. FIG. 3 illustrates samples in which (a) MNP matting is observed, suggesting that a patient is sick (e.g., currently infected; showing symptoms of illness or about to show symptoms soon), (b) MNP matting is not observed, suggesting that a patient is healthy (e.g., currently not infected; no symptoms of illness or recovering from previous illness), and (c) MNP matting is not observed in a blank/control sample.

The following extraction procedure is designed for a sputum sample, but can be used for other biological material samples of similar consistency: (1) Add 1 mL of each sputum sample to a 2-mL sample tube. (2) Add 100 µL of 5 mg/mL MNP to the tube. Close the tube and mix 20× gently. (Keep the tube closed until step 6 to avoid exposure to possible pathogens in the sample). (3) Let stand for 5 min. (4) Mix 20× to mix again and tap/flick downward to collect all of the fluid to the bottom of the tube. (5) Place the tube in a magnetic separator and let stand for 5 min or until MNP separation is observed. (6) Open the tube and remove the supernatant using a pipette. Keep the tip at the front end of the tube (away from MNP) and stay barely below the fluid surface while drawing the supernatant. (7) Remove the tubes from the magnetic separator and close them. Observe the area covered by the MNP mat to detect/diagnose whether one or more biological target analytes were present in the original sample based on formation of a visible nanoparticle mat (e.g., analytes present) or absence thereof (e.g., analytes not present). (8) If desired as a means for confirmation and/or biological target analyte identification, use 10 µL of the matted sample to perform a second assay such as smear microscopy or DNA detection.

Example 5—Pathogen Extraction and Detection Using MNP

The following materials are used to extract and detect biological target analytes using a functionalized magnetic nanoparticle (MNP) composition according to the disclosure:
(a) Protein A from *S. aureus* (Sigma); (b) antibody specific to target analyte; (c) Alkaline gold nanoparticles (AuNP or Au); (d) functionalized magnetic nanoparticle (MNP) composition according to the disclosure as an aqueous dispersion (e.g., at a concentration of 5 mg MNP/mL of dispersion), for example chitosan-coated magnetic nanoparticles according to Example 1 above as well as other MNP compositions according to the Examples 1-3 or the general disclosure; (e) 0.01 M PBS (pH 7.4) (1×PBS); (f) 0.01 M PBS w/0.1% (w/v) BSA (bovine serum albumin); (g) 1 M HCl solution; and (h) Bacterial serial dilutions in 0.01 M PBS.

The following procedures are used for sample preparation, analyte extraction, and/or analyte detection:

Sample (Bacterial) Dilution: Prepare bacterial culture and serially dilute bacterial culture into $10^{-1}$, $10^{-2}$, $10^{-3}$, $10^{-4}$, $10^{-4}$, $10^{-5}$, $10^{-6}$, $10^{-7}$ dilutions.

Sample Preparation: (1) Weigh 25 g of solid sample and place in stomacher bag or measure 99 ml of liquid sample and place in a 250-ml jar. (2) Take 1 ml of $10^{-4}$ serial dilution and inoculate it in the matrix (solid or liquid). (3) Let the inoculated sample stand for 1 hour (e.g., in a biosafety cabinet or on the bench area). (4) For solid samples, add 74 ml of buffered peptone water to the bag. For liquid samples, do not add peptone water. (5) Macerate sample for 2 min in a stomacher. (6) Transfer supernatant into a 250-ml jar.

Sample/Analyte Extraction with MNP: (1) Add 1 ml of MNP in the sample jar. (2) Manually invert the jar 10 times, let stand for 5 min, and invert 10 times again or until well mixed. (3) Magnetically separate (e.g., with an external magnet; for about 30 seconds or more depending on the matrix) the MNP-cell complex and remove the supernatant. Discard waste as biohazard. Remove tube from the magnetic rack. (4) Re-suspend the MNP-cell complex in 1 ml of 0.01 M PBS. (5) Manually invert the tube 10 times. (6) Take 100-µl sample for plating on appropriate agar. Perform a replicate.

Analyte (Bacterial) Detection: (1) From the MNP-extracted sample above, transfer 100 µl to a new 2-mL tube and add 100 µl of 0.01 M PBS with 0.1% (w/v) BSA. (2) Pipette mix gently 10 times. (3) Magnetically separate the BSA-blocked MNP-cell complex. Remove the supernatant. Remove the tube from the magnet. (4) Add 60 µl of 0.01 M PBS and re-suspend gently (by tapping several times the bottom end of the tube). (5) Add 40 µl of an antibody-gold nanoparticle (Ab-Au or Ab-AuNP) conjugate and pipette mix gently (by using pipette tip mixing). (6) Let stand 10 min and pipette mix again. (7) Magnetically separate the MNP-cell-Ab-Au complex by tilting the tube and drawing out the supernatant while still in the magnetic rack. Remove the tube from the magnet. (8) Wash the complex by adding 100 µl of 0.01 M PBS and re-suspend gently. (9) Magnetically separate the MNP-cell-Ab-Au complex. Remove the supernatant. Remove the tube from the magnet. (10) Re-suspend gently in 100 µl of 1M HCl and incubate for 5 min. (11) With −1 min left in 5 min incubation, apply 100 µl of the MNP-cell-Ab-Au-HCl solution evenly onto a screen-printed carbon electrode (SPCE) which is connected to a potentiostat. (12) At the end of 5 min incubation, perform potentiometric analysis and start 2 min oxidation scan (E0=0, E1=+1.5 V, t0=0, t1=120 s). Then run differential pulse voltammetry (DPV) scans from +1.5 V to −1.5 V (E1=+1.5V, Ev=−1.5V, PH/PW=0.05 V for 50 ms, SH=10 mV, ST=300 ms).

Formation of Antibody-Gold Nanoparticle Conjugate: (1) In a 2-ml V-shaped (bottom) microcentrifuge tube, add 500 µl of gold nanoparticles (Au or AuNP). (2) Centrifuge at 18,000 RCF (relative centrifugal force) and 4° C. for 15 min. (3) After centrifugation, remove supernatant as much as possible while leaving a small layer of liquid above the AuNP. (4) Sonicate for 15 min. (5) Add 500 µL of Protein A (0.25 mg/mL) and mix gently (by using gentle pipette tip mixing). (6) Hybridize on a shaker for 1 hour (e.g., using a VWR Mini shaker with set speed at 350). (7) Centrifuge for 12 min at 18,000 RCF and 4° C. (8) Remove supernatant as much as possible while leaving gold in liquid state. (9) Prepare target-specific antibody (Ab) into 1 mg/mL aliquots and add 200 µL (1 mg/mL) of Ab and 200 µL of 0.01 M PBS and mix gently. (10) Conjugate Ab and AuNP on shaker for 1 hour. (11) Add slowly 200 µL of 0.1% (w/v) BSA in 0.01 M PBS and re-suspend gently by tapping several times the bottom end of the tube, which blocks and stabilizes the AuNP labeling of the Ab. (12) Conjugate Ab and AuNP on shaker for 30 min at speed of 250. (13) Centrifuge for 15 min at 18,000 RCF and 4° C. (14) Remove supernatant as much as possible while leaving gold in liquid state. (15) Re-suspend gently in 500 µL of 0.1% BSA in 0.01 M PBS. Final concentration is 0.4 mg Ab/mL AuNPs suspended in 500 µL PBS/BSA. (May change to 1 ml PBS/BSA. This will become 0.2 mg Ab/mL AuNPs suspended in 1 ml of PBS/BSA.)

Formation of Antibody-MNP Conjugate: The following procedure can be used if it is desired to further functionalize the MNP according to the disclosure with a target-specific antibody: (1) Weigh 2.5 mg of MNP and suspend in 150 µl of 0.1M phosphate buffer in a sterile 2-ml microcentrifuge tube. (2) Sonicate for 15 minutes. (3) Add 100 µl of antibody at 2.5 mg/ml. Final solution contains 1 mg/ml antibody and 10 mg/ml MNP, and total volume is 250 µl. (Ab:MNP ratio is 1:10. Other ratios up to 1:25 may use 200 ul of 0.5 mg/ml Ab, for example.) (4) Hybridize on tube rotator for 5 min. (5) Add 25 µl of 10×PBS, and hybridize on tube rotator for 55 min more. (6) Magnetically separate and remove supernatant. (7) Resuspend in 250 µl of 0.1M tris buffer with 0.01% casein, and let stand 5 min. (8) Magnetically separate and remove supernatant. (9) Resuspend in 250 µl of 0.1M tris buffer with 0.01% casein, and let stand 5 min. (10) Magnetically separate and remove supernatant. (11) Resuspend in 250 µl of 0.1M tris buffer with 0.01% casein, and hybridize on tube rotator for 60 min. (12) Magnetically separate and remove supernatant. (13) Resuspend the MNP-F1-Ab in 2.5 ml of 0.1M PBS. (14) Store at 4° C. Use as-is (1 mg/ml Ab, 10 mg/ml MNP), or dilute in half (0.5 mg/ml Ab) before use.

Example 6—Extraction Efficiency of Pathogens from Test Matrix

Chitosan-coated magnetic nanoparticles (Chi-MNP), cysteine-coated magnetic nanoparticles (Cys-MNP), mannose-coated magnetic nanoparticles (Man-MNP), and lysine-coated magnetic nanoparticles (Lys-MNP) according to the disclosure and formed as described above in Example 1 were tested as described above for extraction efficiency of *M. smegmatis* (a surrogate for *M. tuberculosis*), *E. coli* O157:H7, and *E. coli* C3000 in PBS at a spiked concentration of $10^3$ cfu/ml. Extraction results are shown in Table 1 below.

TABLE 1

Extraction Efficiency of Pathogens from Test Matrix

| Bacteria | Chi-MNP | Cys-MNP | Man-MNP | Lys-MNP |
|---|---|---|---|---|
| E. coli C3000 (Gram negative) | 74% | 88% | 0% | 83% |
| E. coli O157:H7 (Gram negative) | 79% | 76% | 0% | |
| M. smegmatis (Gram positive) | 99% | 86% | 95% | 98% |

Example 7—Extraction Efficiency of Pathogens from Artificial Sputum

Chitosan-coated magnetic nanoparticles (Chi-MNP) according to the disclosure and formed as described above in Example 1 were tested as described above for extraction efficiency of *M. smegmatis* (a surrogate for *M. tuberculosis*) in artificial sputum at spiked concentrations of $10^0$, $10^1$, and $10^2$ cfu/ml. Extraction results are shown in Table 2 below.

TABLE 2

Extraction Efficiency of Pathogens from Artificial Sputum

| Bacteria | Concentration | Chi-MNP |
|---|---|---|
| M. smegmatis (Gram positive) | $10^2$ cfu/ml | 90% |
| | $10^1$ cfu/ml | 91% |
| | $10^0$ cfu/ml | 91% |

Example 8—Extraction Efficiency of Pathogens from Food Matrices

Chitosan-coated magnetic nanoparticles (Chi-MNP) according to the disclosure and formed as described above in Example 1 were tested for extraction efficiency of *Salmonella enteritidis* in egg yolk or mayonnaise at spiked concentrations of $10^1$, $10^2$, $10^3$, and $10^5$ cfu/ml. Briefly, 25 g of egg yolk or mayonnaise were inoculated with 10-fold serial dilutions of *Salmonella Enteritidis* and 2 ml of Chi-MNP. 200 mL of buffered peptone water (BPW) were added and samples were mixed. Samples were magnetically separated for 15 min, washed with BPW, and concentrated 100-fold. Samples were plated on Brilliant Green Agar (BGA), incubated at 37° C. for 24 hours and cells counted. Extraction results are shown in Table 3 below.

TABLE 3

Extraction Efficiency of Pathogens from Food Matrices

| Bacteria | Matrix/Concentration | Chi-MNP |
|---|---|---|
| S. enteritidis | Mayonnaise at $10^5$ cfu/ml | 61% |
| | Egg Yolk at $10^5$ cfu/ml | 98% |
| | Egg Yolk at $10^3$ cfu/ml | 99% |
| | Egg Yolk at $10^2$ cfu/ml | 99% |
| | Egg Yolk at $10^1$ cfu/ml | 97% |

Example 9—Extraction Efficiency of Pathogens from Drinking Water

Chitosan-coated magnetic nanoparticles (Chi-MNP) according to the disclosure and formed as described above in Example 1 were tested as described above for extraction efficiency of *E. coli* C3000 tap drinking water at spiked concentrations of 0.7, $10^3$, and $10^4$ cfu/ml. Extraction results after washing are shown in Table 4 below.

TABLE 4

Extraction Efficiency of Pathogens from Drinking Water

| Bacteria | Concentration | Chi-MNP |
|---|---|---|
| E. coli C3000 (Gram negative) | $10^4$ cfu/ml | 99% |
| | $10^3$ cfu/ml | 105% |
| | 0.7 cfu/ml | 98% |

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compounds, compositions, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

What is claimed is:

1. A method for extracting a biological target analyte from a sample, the method comprising:
    (a) providing a functionalized magnetic particle composition comprising (i) a magnetic particle core, and (ii) a biomimetic binding pair member bound to an external surface of the magnetic particle core, the binding pair member comprising a N-acetylglucosamine moiety and being capable of non-specific binding to a plurality of biological target analytes, wherein the binding pair member comprising the N-acetylglucosamine moiety comprises a pyrolysis by-product of chitosan and optionally one or more of an oligomeric unit of chitosan and a monomeric unit of chitosan;
    (b) contacting the functionalized magnetic particle composition with a sample containing or suspected of containing one or more biological target analytes to which the binding pair member of the functionalized magnetic particle composition is capable of non-specific binding for a time sufficient to bind any biological target analytes in the sample to the functionalized magnetic particle composition, thereby forming a magnetic particle-analyte conjugate; and
    (c) magnetically separating the magnetic particle-analyte conjugate from the sample.

2. The method of claim 1, wherein part (b) comprises contacting the functionalized magnetic particle composition with the sample for a period ranging from 1 minute to 30 minutes before magnetically separating in part (c).

3. The method of claim 1, wherein the sample comprises a biological material.

4. The method of claim 1, wherein the sample is selected from the group consisting of saliva, sputum, urine, blood, cerebrospinal fluid, tracheal swabs, and combinations thereof.

5. The method of claim 1, wherein the sample comprises a food item.

6. The method of claim 1, wherein the sample is selected from the group consisting of vegetables, fruits, eggs, poultry, fish, seafood, milk, mayonnaise, components thereof, and combinations thereof.

7. The method of claim 1, further comprising:
(d) detecting a specific biological target analyte in the magnetic particle-analyte conjugate.

8. The method of claim 1, further comprising:
(d) detecting a non-specific biological target analyte in the magnetic particle-analyte conjugate.

9. The method of claim 1, wherein the magnetic particle core comprises at least one of Fe(II) and Fe(III).

10. The method of claim 1, wherein the binding pair member comprises at least one of a glycan and glycoconjugate.

11. The method of claim 1, wherein the binding pair member further comprises at least one of a N-acetylgalactosamine moiety, a N-acetylneuraminic acid moiety, a glucose moiety, a galactose moiety, a fucose moiety, a mannose moiety, a rhamnose moiety, a glucuronic acid moiety, a galacturonic acid moiety, an arabinofuranose acid moiety, and a xylose moiety.

12. The method of claim 1, wherein the binding pair member comprising the N-acetylglucosamine moiety comprises the oligomeric unit of chitosan, the monomeric unit of chitosan, and the pyrolysis by-product of chitosan.

13. The method of claim 12, wherein:
the oligomeric unit of chitosan comprises acetylated and deacetylated oligomeric units containing 2 to 20 chitosan monomeric units;
the monomeric unit of chitosan comprises acetylated chitosan monomeric units and deacetylated chitosan monomeric units; and
the pyrolysis by-product of chitosan comprises one or more of carbon, carbon nitride, and aminated carbon.

14. The method of claim 1, wherein the binding pair member comprises:
a first binding pair member comprising the N-acetylglucosamine moiety; and
a second binding pair member comprising at least one of a carboxyl moiety and an amino acid moiety.

15. The method of claim 14, wherein the second binding pair member comprises at least one of a cysteine moiety, a methionine moiety, a glycine moiety, and a lysine moiety.

16. The method of claim 14, wherein the second binding pair member comprises at least one of a carboxylic acid moiety and a carboxylate salt moiety.

17. The method of claim 1, wherein the biological target analytes are selected from the group consisting of bacteria, viruses, proteins, and combinations thereof.

18. The method of claim 1, wherein the biological target analytes comprise one or more of *Mycobacterium tuberculosis, Mycobacterium smegmatis, Escherichia coli, Salmonella enteritidis, Listeria monocytogenes, Vibrio cholera, Bacillus cereus*, Dengue virus, influenza virus, and Newcastle disease virus.

19. The method of claim 1, wherein the binding pair member is covalently bound to the magnetic particle core.

20. The method of claim 1, wherein the functionalized magnetic particle composition has a particle size ranging from 50 nm to 1000 nm.

21. The method of claim 1, wherein a weight ratio of the magnetic particle core to the biomimetic binding pair member ranges from 4:1 to 1:4.

22. The method of claim 1, wherein the functionalized magnetic particle composition is in the form of a particulate powder.

23. The method of claim 1, wherein:
the functionalized magnetic particle composition (iii) water; and
the water provides a suspending medium for a plurality of functionalized magnetic particles comprising the magnetic particle cores and the biomimetic binding pair member bound thereto in the form of a dispersion.

24. The method of claim 23, wherein the functionalized magnetic particles are present in the suspending medium at a concentration ranging from 0.01 g/L to 100 g/L.

25. The method of claim 1, wherein the functionalized magnetic particle composition is free from specific binding pair members.

26. A method for extracting a biological target analyte from a sample, the method comprising:
(a) providing a functionalized magnetic particle composition comprising (i) a magnetic particle core comprising at least one of Fe(II) and Fe(III); and (ii) a biomimetic binding pair member bound to an external surface of the magnetic particle core, the binding pair member comprising a N-acetylglucosamine moiety and being capable of non-specific binding to a plurality of biological target analytes, wherein the binding pair member comprising the N-acetylglucosamine moiety comprises the oligomeric unit of chitosan, the monomeric unit of chitosan, and the pyrolysis by-product of chitosan;
(b) contacting the functionalized magnetic particle composition with a sample containing or suspected of containing one or more biological target analytes to which the binding pair member of the functionalized magnetic particle composition is capable of non-specific binding for a time sufficient to bind any biological target analytes in the sample to the functionalized magnetic particle composition, thereby forming a magnetic particle-analyte conjugate; and
(c) magnetically separating the magnetic particle-analyte conjugate from the sample;
wherein:
the functionalized magnetic particle composition has a particle size ranging from 100 nm to 1000 nm.

27. The method of claim 26, wherein:
the oligomeric unit of chitosan comprises acetylated and deacetylated oligomeric units containing 2 to 20 chitosan monomeric units;
the monomeric unit of chitosan comprises acetylated chitosan monomeric units and deacetylated chitosan monomeric units; and
the pyrolysis by-product of chitosan comprises two or more of carbon, carbon nitride, and aminated carbon.

* * * * *